(12) United States Patent
Wescott et al.

(10) Patent No.: US 11,311,885 B2
(45) Date of Patent: Apr. 26, 2022

(54) SYSTEM AND METHOD FOR CONFINING REAGENTS WITHIN A FLUIDIC DEVICE

(71) Applicant: Integrated Nano-Technologies, Inc., Henrietta, NY (US)

(72) Inventors: Nathaniel E. Wescott, West Henrietta, NY (US); Dennis M. Connolly, Rochester, NY (US); Mark J. Smith, Rochester, NY (US)

(73) Assignee: Integrated Nano-Technologies, Inc., Henrietta, NY (US)

( * ) Notice: Subject to any disclaimer, the term of this patent is extended or adjusted under 35 U.S.C. 154(b) by 491 days.

(21) Appl. No.: 16/306,194

(22) PCT Filed: Jun. 2, 2017

(86) PCT No.: PCT/US2017/035671
§ 371 (c)(1),
(2) Date: Nov. 30, 2018

(87) PCT Pub. No.: WO2017/210552
PCT Pub. Date: Dec. 7, 2017

(65) Prior Publication Data
US 2020/0139374 A1  May 7, 2020

Related U.S. Application Data

(60) Provisional application No. 62/344,537, filed on Jun. 2, 2016.

(51) Int. Cl.
*G01N 1/00* (2006.01)
*B01L 3/00* (2006.01)

(52) U.S. Cl.
CPC ............... *B01L 3/527* (2013.01); *B01L 3/502* (2013.01); *B01L 2200/12* (2013.01); *B01L 2200/16* (2013.01); *B01L 2300/042* (2013.01); *B01L 2300/047* (2013.01); *B01L 2300/06* (2013.01); *B01L 2300/0681* (2013.01); *B01L 2300/0832* (2013.01)

(58) Field of Classification Search
CPC .................. B01L 3/50; B01L 2200/01; B01L 2300/0681; G01N 1/30; G01N 1/405
USPC ......................................... 436/174, 176, 178
See application file for complete search history.

(56) References Cited

U.S. PATENT DOCUMENTS

| | | | |
|---|---|---|---|
| 8,790,932 B2 | 7/2014 | Augstein et al. | |
| 2005/0112023 A1 | 5/2005 | Liang | |
| 2007/0219366 A1 | 9/2007 | Gumbrecht et al. | |
| 2009/0008395 A1 | 1/2009 | Sattler et al. | |
| 2010/0044918 A1* | 2/2010 | Lee | B29C 39/10 264/297.8 |
| 2014/0099646 A1 | 4/2014 | Connolly et al. | |

OTHER PUBLICATIONS

PCT/US2017/035671 filed Jun. 2, 2017; International Search Report dated Aug. 29, 2017; Integrated Nano-Technologies, Inc.; 3 pages.
PCT/US2017/035671 filed Jun. 2, 2017; International Search Report/ Written Opinion; dated Aug. 29, 2017; Integrated Nano-Technologies, Inc.; 11 pages.
PCT/US2017/035671 filed Jun. 2, 2017; International Preliminary Report on Patentability; dated Dec. 4, 2018; Integrated Nano-Technologies, Inc.; 8 pages.

* cited by examiner

*Primary Examiner* — Natalia Levkovich
(74) *Attorney, Agent, or Firm* — Sterne, Kessler, Goldstein & Fox P.L.L.C.

(57) ABSTRACT

A method for inserting and retaining a reagent within a disposable cartridge of a diagnostic assay system. The method includes the steps of: (i) drying a reagent in combination with a carrier, and (ii) inserting the carrier, with the dried reagent, into an open end of one of the assay chambers, wherein the carrier facilitates insertion of the pellet into a chamber without contact by an operator.

8 Claims, 7 Drawing Sheets

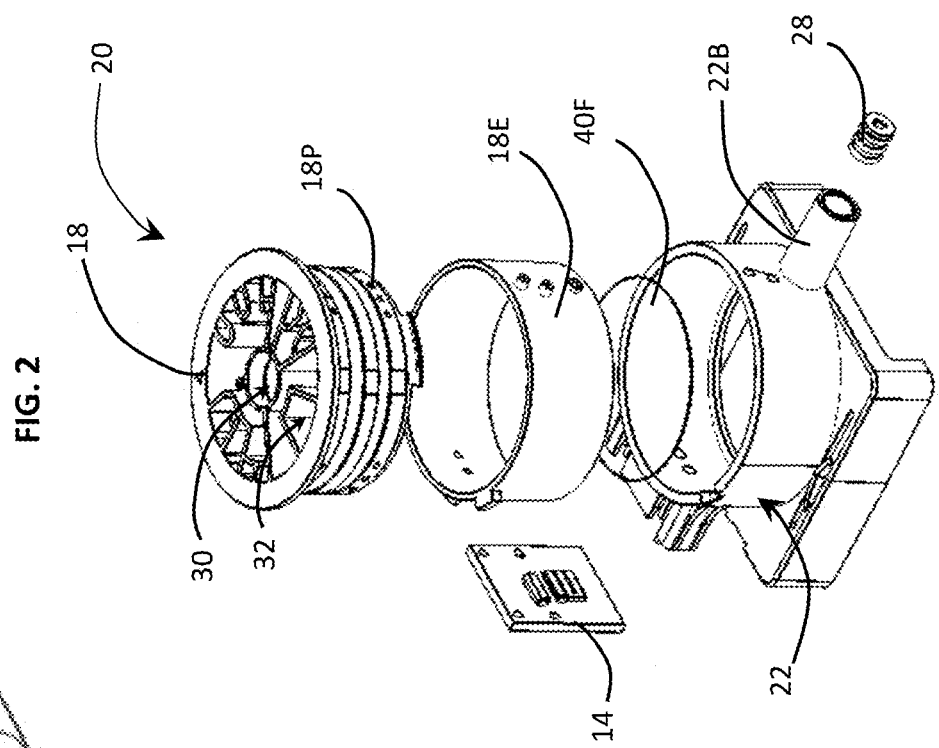
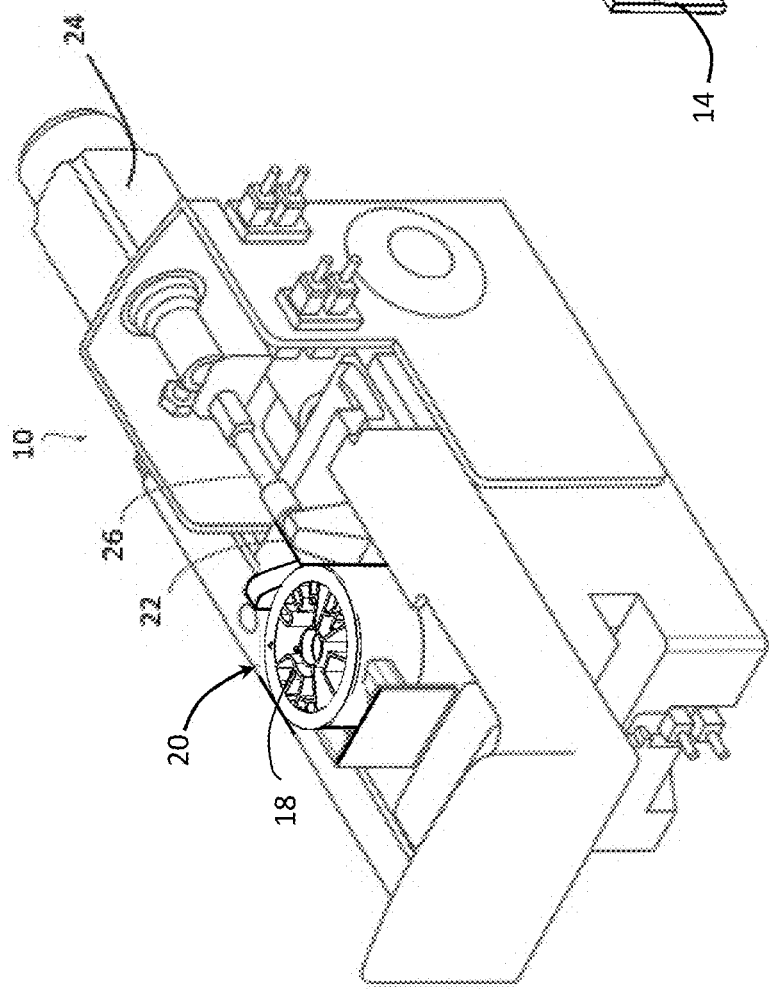

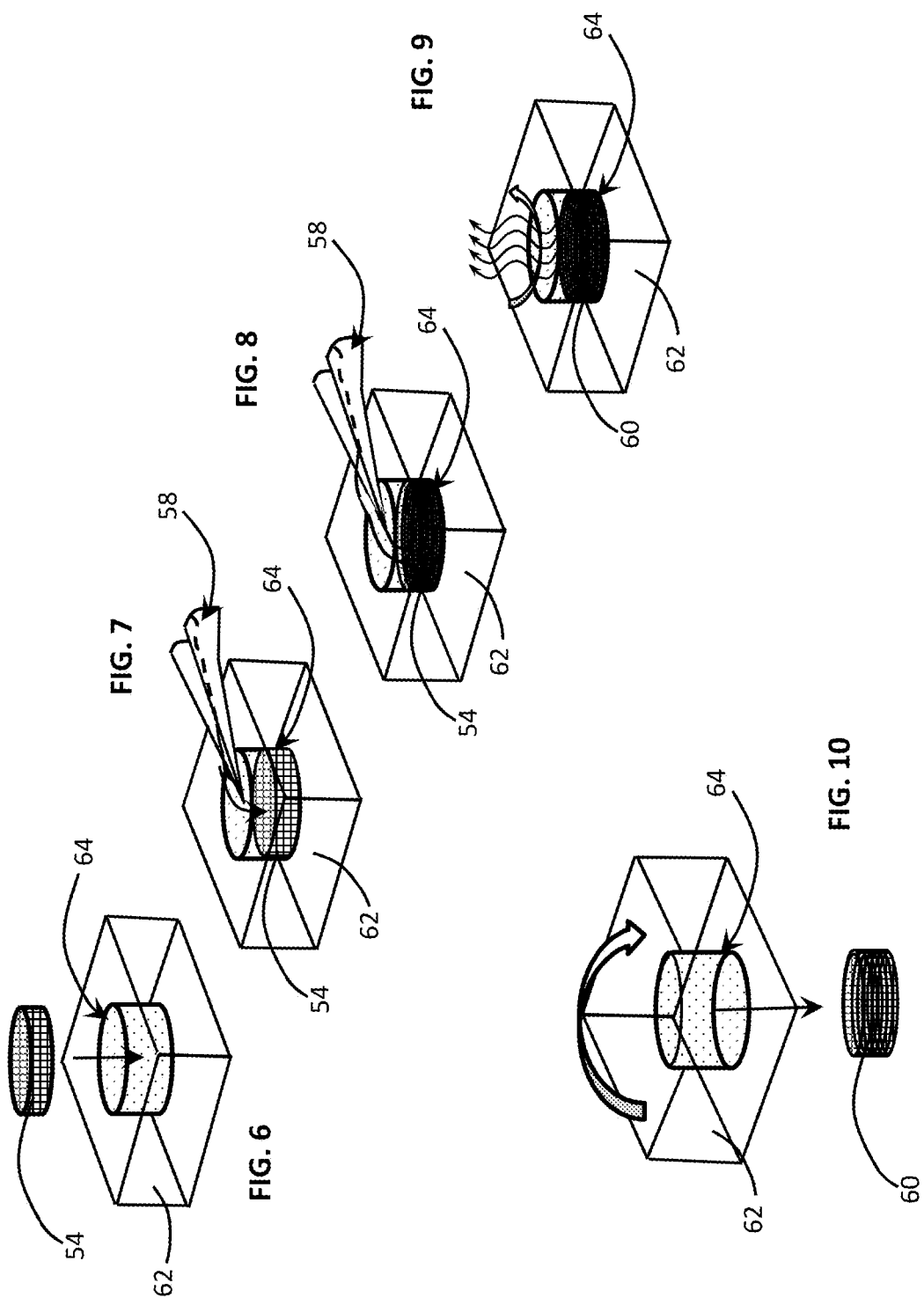

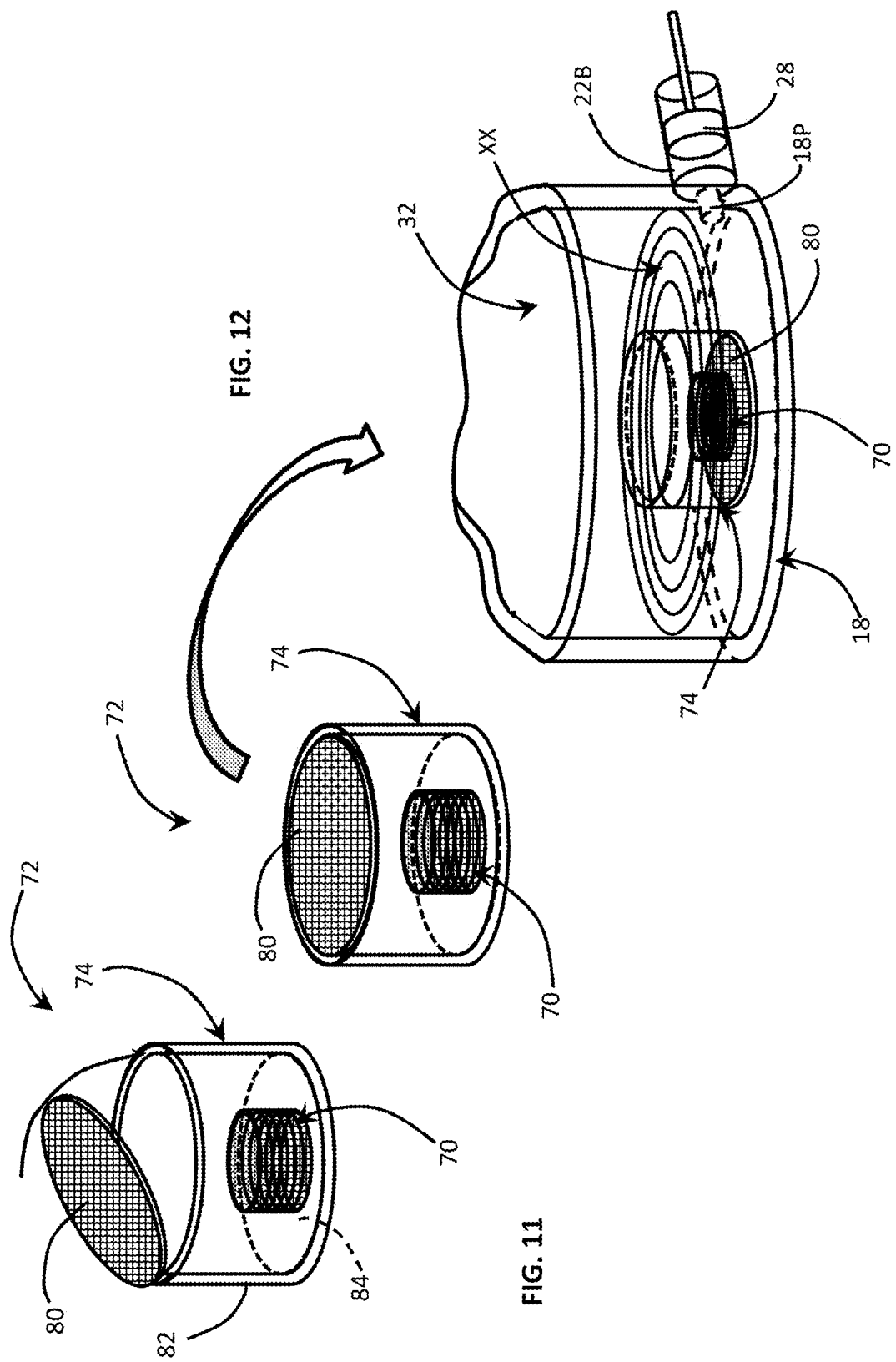

SYSTEM AND METHOD FOR CONFINING REAGENTS WITHIN A FLUIDIC DEVICE

CROSS-REFERENCE TO RELATED APPLICATIONS

This application is a Non-Provisional Utility patent application which claims priority to U.S. Provisional Patent Application Ser. No. 62/344,537 filed Jun. 2, 2016 entitled "Methods to Confine Dried Reagents within a Fluidic Device." The contents of the aforementioned applications are hereby incorporated by reference in their entirety.

This application also relates to international patent application PCT/US2017/032904 internationally filed May 16, 2017 entitled "Flow Control System for Diagnostic Assay System," which claims priority to U.S. Provisional Patent Application Ser. No. 62/337,446 filed May 17, 2016 entitled "Multi-Chamber Rotating Valve and Cartridge." Additionally, this application also relates to U.S. patent application Ser. No. 15/157,584 filed May 18, 2016 entitled "Method and System for Sample Preparation" which is a continuation of U.S. Non-Provisional patent application Ser. No. 14/056,543, filed Oct. 17, 2013, now U.S. Pat. No. 9,347,086, which claims priority to U.S. Provisional Patent Application Ser. No. 61/715,003, filed Oct. 17, 2012, which is a continuation-in-part of U.S. patent application Ser. No. 12/785,856, filed May 24, 2010, now U.S. Pat. No. 8,663,918, which claims priority to U.S. Provisional Patent Application Ser. No. 61/180,494, filed May 22, 2009, and which is also a continuation-in-part of U.S. patent application Ser. No. 12/754,205, filed Apr. 5, 2010, now U.S. Pat. No. 8,716,006, which claims priority to U.S. Provisional Patent Application Ser. No. 61/158,519, filed Apr. 3, 2009. The contents of the aforementioned applications are hereby incorporated by reference in their entirety.

FIELD OF THE INVENTION

The present invention relates to a disposable cartridge for a portable diagnostic assay device, and more particularly, to a system and method for producing and confining dried reagents in one of the chambers of the disposable cartridge for subsequent rehydration during assay testing.

BACKGROUND OF THE INVENTION

Fluid analysis of biological samples such as blood and food samples for assay testing generally requires a series of process steps. These steps generally require that particular fluids contact a reaction area at different times and in varying secession. Furthermore, each fluid may require different pre-treatment prior to contacting the reaction area such as chemical, optical, thermal, mechanical, magnetic or acoustical pre-treatment. A single fluid sample may be subjected to a variety of steps prior to contact with a reaction area such as heating or ultrasonic processing. As the number of fluids and pre-treatment steps increase, the fluid delivery system becomes more complex.

One of the more recent developments in the field of diagnostic testing relates to a portable diagnostic assay device capable of performing a variety of common and complex laboratory procedures without the requirement for a staff of highly-skilled technicians to perform these procedures in a costly laboratory environment/setting. The portable diagnostic assay device and related diagnostic cartridges are disclosed in a portfolio of issued and pending U.S. and foreign patents/patent applications assigned to Integrated Nano-Technologies located in the town of Henrietta, state of New York, USA. The portable diagnostic assay device comprises a small base unit, i.e., generally smaller than a standard briefcase, for accepting one of many distinct, dedicated, and disposable cartridges prepared for conducting a single assay test. For example, the disposable cartridges may be prepared for testing blood borne diseases, food borne bacteria, and/or animal/insect carrying bacteria and viruses.

The diagnostic cartridges comprise a plurality of chambers each containing a reagent used in the assay test, e.g., PCR primers, enzymes and certain chemical compounds. To maximize shelf life and reliability, these reagents are typically dehydrated/lyophilized and sealed within the chambers of the diagnostic cartridge. During storage, handling and transport, the dried reagents can break apart such that a film of powder coats the internal chamber, as well as the ports and channels leading to and from the chamber. Inasmuch as each gram of reagent is needed to ensure reliable/consistent test results, it will be appreciated that any unused or inaccessible portion of reagent, e.g., a portion which remains logged in a corner of a chamber or disposed in a vent port, can adversely impact the test results.

There is, therefore, a need for a system and method for confining a reagent in a disposable cartridge for a portable diagnostic assay device which facilitates complete admixture of the confined reagent with a solvent, fluid reagent or other fluid assay chemical injected into, or withdrawn from, an assay chamber.

SUMMARY OF THE INVENTION

In one embodiment, a method is provided for retaining a reagent within a disposable cartridge of a diagnostic assay system. The method includes the steps of: (i) drying a reagent within a carrier configured to be received within an open end of one of the assay chambers, and (ii) inserting the carrier, including the pellet of dried reagent, into an open end of the assay chamber, wherein the carrier facilitates insertion of the pellet into a chamber without contact by an operator.

In another embodiment, a method comprises (i) drying a reagent in combination with a carrier configured to be received within an open end of one of the assay chambers, and (ii) the carrier, including the dried reagent, is inserted into an open end of the assay chamber, wherein the carrier facilitates insertion of the pellet into a chamber without contact by an operator.

In another embodiment, the method comprises the steps of: (i) producing a scaffold structure having a geometric shape approximating the shape of a portion of the least one assay chamber, (ii) mixing a reagent, a binder and a liquid solvent, (iii) impregnating the scaffold structure with the liquid reagent-binder, and (iv) drying the liquid reagent-binder to remove the solvent thereby producing a dried reagent having the geometric shape corresponding to the shape of the assay chamber.

In yet another embodiment, a disposable cartridge is provided comprising: (i) a cartridge body defining a syringe barrel having a barrel port operative to inject and withdraw assay fluids in response to displacement of a syringe plunger; (ii) a cartridge rotor comprising: a plurality of assay chambers rotatable about an axis and mounted for rotation to the cartridge body, the cartridge rotor defining a port disposed in fluid communication with at least one of the assay chambers and rotated into alignment with the barrel port of the syringe barrel, and (iii) a carrier disposed in one of the assay chambers, configured to secure a dehydrated reagent, and facilitating rehydration of the reagent upon the introduction of a fluid solvent into the assay chamber.

BRIEF DESCRIPTION OF THE DRAWINGS

The present invention is disclosed with reference to the accompanying drawings, wherein:

FIG. 1 is a perspective view of a portable diagnostic assay system operative to accept one of a plurality of disposable cartridges configured to test samples of collected blood/food/biological materials.

FIG. 2 is an exploded perspective view of one of the disposable cartridges configured to test the blood/food/biological materials.

FIGS. 6-10 depict schematic perspective views of various method steps which may be necessary to prepare an assay chamber for a dissolvable assay material, pellet, sphere, pill or container including the steps of: (i) forming a support scaffold in a geometric shape which is supported within and captured by a portion of an assay chamber (FIG. 6), (ii) inserting the support scaffold in a fluid container approximating the geometric shape of the assay chamber (FIG. 7), (iii) loading the support scaffold with an assay material which has been dissolved in a flowable solvent (FIG. 8), (iv) dehydration or lyophillization of the assay material in combination with the support scaffold (FIG. 9), and, (v) transferring the support scaffold (loaded with assay material) into the assay chamber of the disposable cartridge (see FIG. 10).

FIG. 11 depicts an isolated perspective view of another embodiment of the disclosure wherein an assay chemical is prepared for handling and transport within a carrier pod or container having an end suitable for receiving and mixing the assay chemicals of one chamber with the assay chemicals of another chamber.

FIG. 12 depicts the carrier pod having a screened- or filtered-end to allow mixture of the assay chemicals/fluids when the filtered-end of the carrier pod is placed face down in the assay chamber for receipt of injected assay chemicals by a syringe barrel of the disposable cartridge.

Corresponding reference characters indicate corresponding parts throughout the several views. The examples set out herein illustrate several embodiments of the invention but should not be construed as limiting the scope of the invention in any manner.

DETAILED DESCRIPTION

Figure 4:
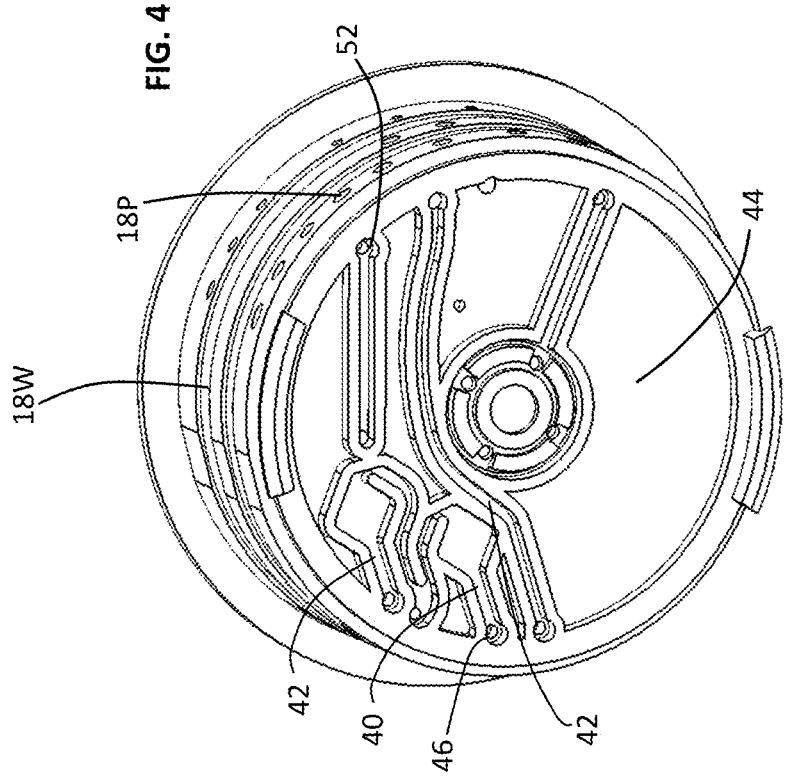
FIG. 4 is a bottom view of the disposable cartridge shown in FIG. 3 illustrating a variety of channels operative to move at least a portion of the assay material from one chamber to another the purpose of performing multiple operations on the sample.

A disposable cartridge is described for use in a portable/automated assay system such as that described in commonly-owned, co-pending U.S. patent application Ser. No. 15/157,584 filed May 18, 2016 entitled "Method and System for Sample Preparation" which is hereby included by reference in its entirety. While the principal utility for the disposable cartridge includes DNA testing, the disposable cartridge may be used in be used to detect any of a variety of diseases which may be found in either a blood, food or biological specimen. For example, blood diagnostic cartridges may be dedicated cartridges useful for detecting hepatitis, autoimmune deficiency syndrome (AIDS/HIV), diabetes, leukemia, graves, lupus, multiple myeloma, etc., just naming a small fraction of the various blood borne diseases that the portable/automated assay system may be configured to detect. Food diagnostic cartridges may be used to detect salmonella, E-coli, Staphylococcus aureus or dysentery. Insect or animal borne diseases include malaria, encephalitis and the West Nile virus.

More specifically, and referring to FIGS. 1 and 2, a portable assay system 10 receives any one of a variety of disposable assay cartridges 20, each selectively configured for detecting a particular attribute of a fluid sample, each attribute potentially providing a marker for a blood, food or biological (animal borne) disease. The portable assay system 10 includes one or more linear and rotary actuators operative to move fluids into, and out of, various compartments or chambers of the disposable assay cartridge 20 for the purpose of identifying or detecting a fluid attribute. More specifically, a signal processor 14, i.e., a PC board, controls a rotary actuator (not shown) of the portable assay system 10 so as to align one of a variety of ports 18P, disposed about a cylindrical rotor 18, with a syringe barrel 22B of a stationary cartridge body 22. The processor 14 controls a linear actuator 24, to displace a plunger shaft (not shown) so as to develop pressure i.e., positive or negative (vacuum) in the syringe barrel 22. That is, the plunger shaft displaces an elastomer plunger 28 within the syringe 22 to move and or admix fluids contained in one or more of the chambers 30, 32.

The disposable cartridge 20 provides an automated process for preparing the fluid sample for analysis and/or performing the fluid sample analysis. The sample preparation process allows for disruption of cells, sizing of DNA and RNA, and concentration/clean-up of the material for analysis. More specifically, the sample preparation process of the instant disclosure prepares fragments of DNA and RNA in a size range of between about 100 and 10,000 base pairs. The chambers can be used to deliver the reagents necessary for end-repair and kinase treatment. Enzymes may be stored dry and rehydrated in the disposable cartridge, or added to the disposable cartridge, just prior to use. The use of a rotary actuator allows for a single plunger to draw and dispense fluid samples from a single rotary device without the need for a complex system of test tubes, carrier probes, and valves to move in unison or open/close at precise times. This greatly reduces potential for leaks and failure of the device compared to conventional systems. It will also be appreciated that the system greatly diminishes the potential for human error.

Figure 3:
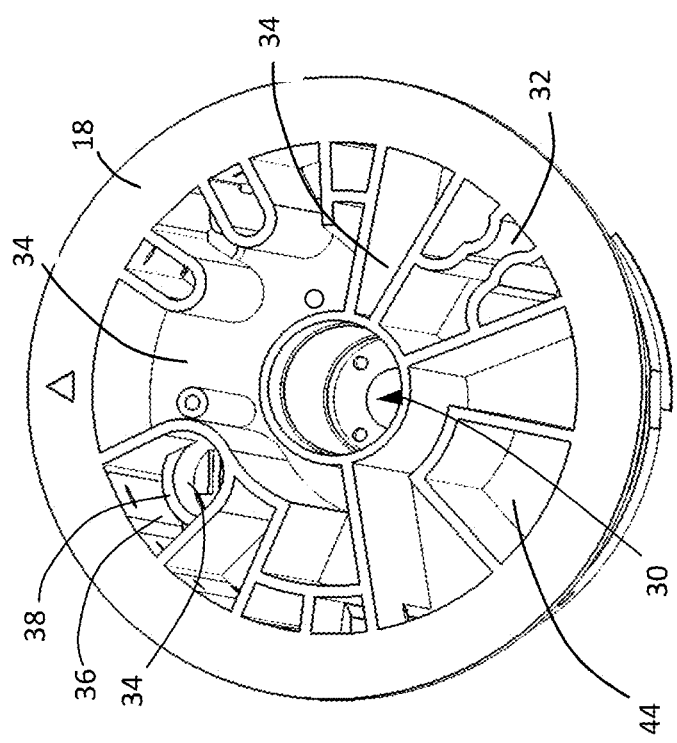
FIG. 3 is a top view of the one of the disposable cartridges illustrating a variety of assay chambers including a central assay chamber for receiving the blood/food/biological material and at least one other chamber containing an assay chemical suitable to breakdown the blood/food/biological material to detect a particular attribute thereof.

In FIGS. 2, 3 and 4, the cylindrical rotor 18 includes a central chamber 30 and a plurality of assay chambers 32, 34 surrounded, and separated by, one or more radial, circumferential or planar walls 18E, 18W, and 40F, respectfully. In the described embodiment, the central chamber 30 receives the fluid sample while the surrounding chambers 32, 34 may contain a premeasured assay chemical or reagent for the purpose of detecting an attribute of the fluid sample. The chemical or reagents may be initially dry and rehydrated immediately prior to conducting a test. Some of the chambers 32, 34 may be open to allow the introduction of an assay chemical while an assay procedure is underway or in-process. The chambers 30, 32, 34, 36, 38 are disposed in fluid communication, e.g., from one of the ports 18P, 46 to one of the chambers 30, 32, 34, by channels 40, 42 molded along a bottom panel 44, i.e., along an underside surface 44S of the rotor 18.

During development of the disposable cartridge and diagnostic assay system, the inventors determined that to maximize shelf life and reliability, reagents such as PCR primers, enzymes and certain chemical compounds must be dehydrated or lyophilized. They also discovered, however, that such dehydration or lyophillization caused damage to the delicate/dried assay chemicals and reduced PCR yield. That is, during loading and handling, the dried assay chemicals tended to break-apart causing a powdered residue to lodge in corners, inlet and outlet ports or other areas where rehydration fluid could not reach. Inasmuch as PCR reactions are logarithmic in scale as a function of mix accuracy, even small deviations can result in poor yield. To address these deficiencies, the inventors discovered a variety of improvements relating to the loading methodology of the reagents to significantly improve the subsequent yield.

Figure 5:
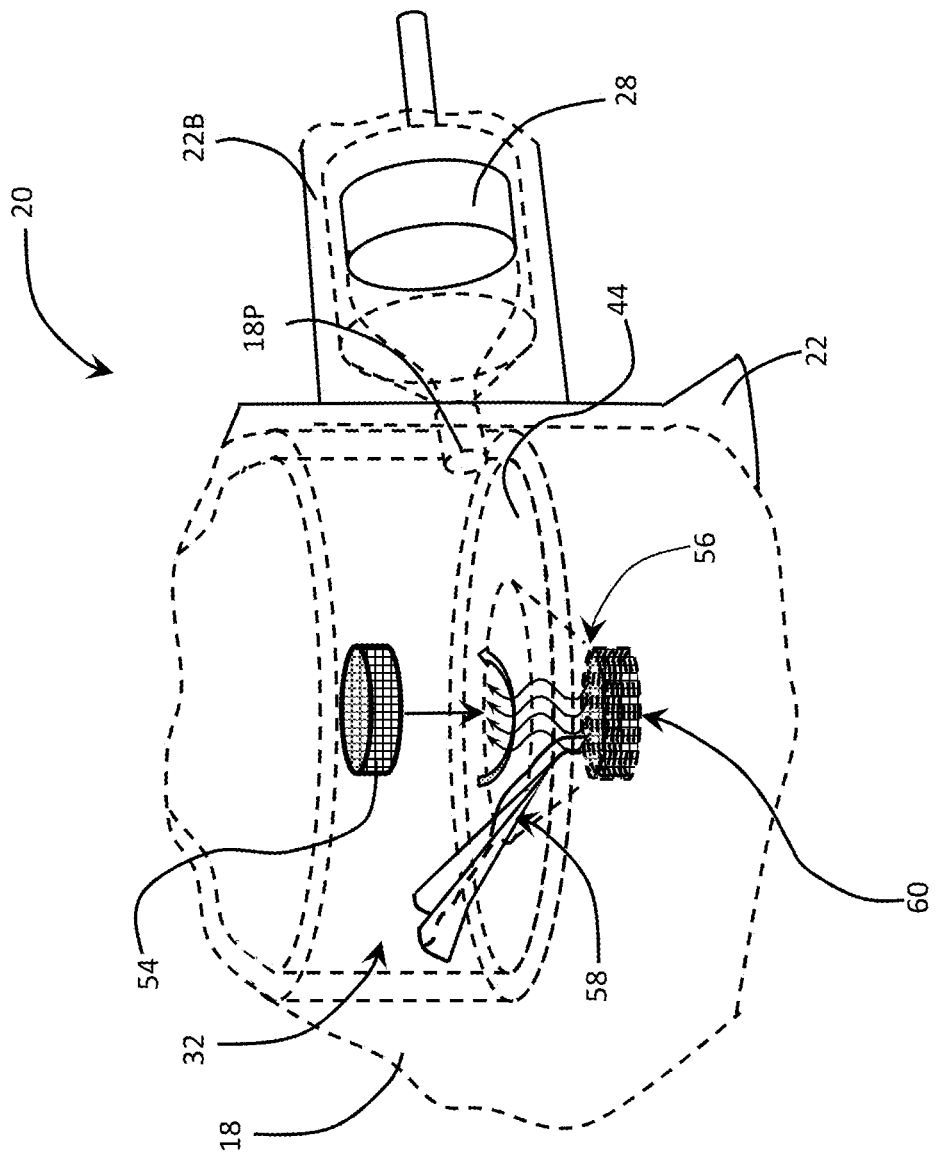
FIG. 5 is a broken-away, cross-sectional, schematic view of an assay chamber being prepared for accepting a dehydrated/lyophilized assay chemical in a sump region of one of the assay chambers.

In one embodiment of the disclosure, and referring to FIG. 5, a method is provided for confining a dried reagent within the disposable cartridge 20 of the diagnostic assay system 10. In this embodiment, a scaffolding structure 54 provides a stabilizing matrix or reinforcement for a dehydrated or lyophilized assay chemical. More specifically, the scaffolding structure 54 is formed in the shape of a portion of the assay chamber 32 which limits or inhibits the lateral motion of the dehydrated or lyophilized assay chemical. The scaffolding structure 54 comprises a matrix of wire, netting or opened-celled foam material and is formed in the shape of a lower sump region/portion 56 of the assay chamber 32. In the described embodiment, the scaffolding structure 54 forms a conically-shaped depression in the bottom portion or panel 44 of the disposable cartridge 20. In the context used herein, a sump region 56 is any low point in a cavity wherein a fluid collects under the influence of gravity.

In a first step of the method, the scaffolding structure 54 is shaped in the form of a cylindrical disc or pellet and inserted into the sump region 56 of the assay chamber 32. Next, an assay chemical, a binder and/or a liquid solvent is combined to produce a flowable, liquid reagent-binder 58. Finally, the scaffold structure 54 is impregnated with the liquid reagent-binder 58 and dried, i.e., via dehydration or lyophillization, to provide shape, form and strength to the dried reagent 60. Preferably, the dried reagent-binder 60 is placed within a portion of the assay chamber 32 which limits the lateral motion of the dried reagent-binder such as within the conically-shaped sump region 56 of the assay chamber 32. Alternatively, the dried reagent 60 may bond to the lower panel 44 of the assay chamber 32 such that the reagent 60 remains stable, i.e., does not move or displace, while the disposable cartridge is shipped during transport.

During use, liquid solvents and/or other liquid assay chemicals are injected into the assay chamber 32 by the syringe barrel 22B of the cartridge body 22. The assay fluid flows into the sump region 56 of the assay chamber 32, inasmuch as the sump region 56 is a low-point in the chamber 32. As a consequence, the assay fluid rehydrates the dried reagent 60 supported by the scaffolding structure 54.

In another embodiment of the method, the scaffolding structure 54, once again, is formed in the shape of a portion of the assay chamber 32. However, rather than being formed in a sump region of the assay chamber 32, a mold or mold container 62 is provided to form, impregnate and transfer the dried reagent 60 into the bottom or sump region 56 of the assay chamber 32. More specifically, FIG. 6 depicts the scaffolding structure 60 being disposed into a mold cavity 64 of the container 62. FIG. 7 depicts a liquid mixture 58 of the reagent, binder and liquid solvent as it is poured into the mold cavity 64. In FIG. 8, the scaffolding structure 60 is impregnated with the liquid mixture 58 while FIG. 9 depicts the dehydration or lyophillization of the impregnated structure 60. Once the impregnated structure 60 is dried, the mold 62 is overturned in FIG. 10 to empty the dried reagent 60 from the mold cavity 64. In this embodiment, the reagent 60 is transferred, placed and/or bonded into the base or sump region 56 of the assay chamber 32. Once again, assay fluids injected into the chamber 32 function to rehydrate the dried reagent 60 of the scaffolding structure 54.

In yet another embodiments, a dried reagent 70 may or may not be reinforced by a scaffolding structure 54. In these embodiments, the dried reagent 70 may simply comprise a reagent bound together by a binding agent, i.e., a glucose binder. Furthermore, a carrier 72 secures or holds the dried reagent in combination with the assay chamber 32 while mitigating, limiting or otherwise minimizing the amount of handling, interaction, or intervention by an operator. As will be discussed in the embodiments disclosed in FIGS. 11 through 15, the carrier 72 may comprise: (i) an enclosed pod 74 having a fluid by-pass filter at one end for rehydrating a pellet of dried reagent 70, (ii) a cap 76 defining a cavity having an open end for accepting a pellet 70, or a removable cover to open and close the open end, or, (iii) a plug-spring 78 having a spring element 90 configured to bias a pellet 70 of dried reagent downwardly into the assay chamber 32.

In FIGS. 11 and 12, the pod 74 encloses the pellet 70 and includes a by-pass filter 80 at one end to facilitate rehydration of the dried reagent, i.e., the dried pellet 70, upon injection of an assay fluid XX into the assay chamber 32. In the described embodiment, the pod 74 may include a tubular sleeve 82 closed at each of its ends 80, 84 to retain the pellet 70 within a relatively small confinement area or volume. The pellet 70 may or may not be reinforced by a scaffolding structure and the tubular sleeve 82 may or may not be dissolvable by the assay fluid XX. Furthermore, the pellet 70 of dried reagent may be formed while in the tubular sleeve 82 or formed externally of the sleeve 82. That is, a mixture of reagent, binder and a solvent may be loaded into the carrier 72 and dehydrated, lyophilized or freeze-dried while in the tubular sleeve of the pod 74.

In the described embodiment, the by-pass filter 80 may be detached from the tubular sleeve 82 to facilitate loading of a pellet 70. Furthermore, to facilitate mixing with the assay fluid XX, the by-pass filter 80 may be over-turned to face downwardly in the assay chamber 32 such that assay fluid XX fill the pod 74 immediately upon injection of the assay fluid XX by the syringe barrel 22B of the cartridge body.

Figure 14:
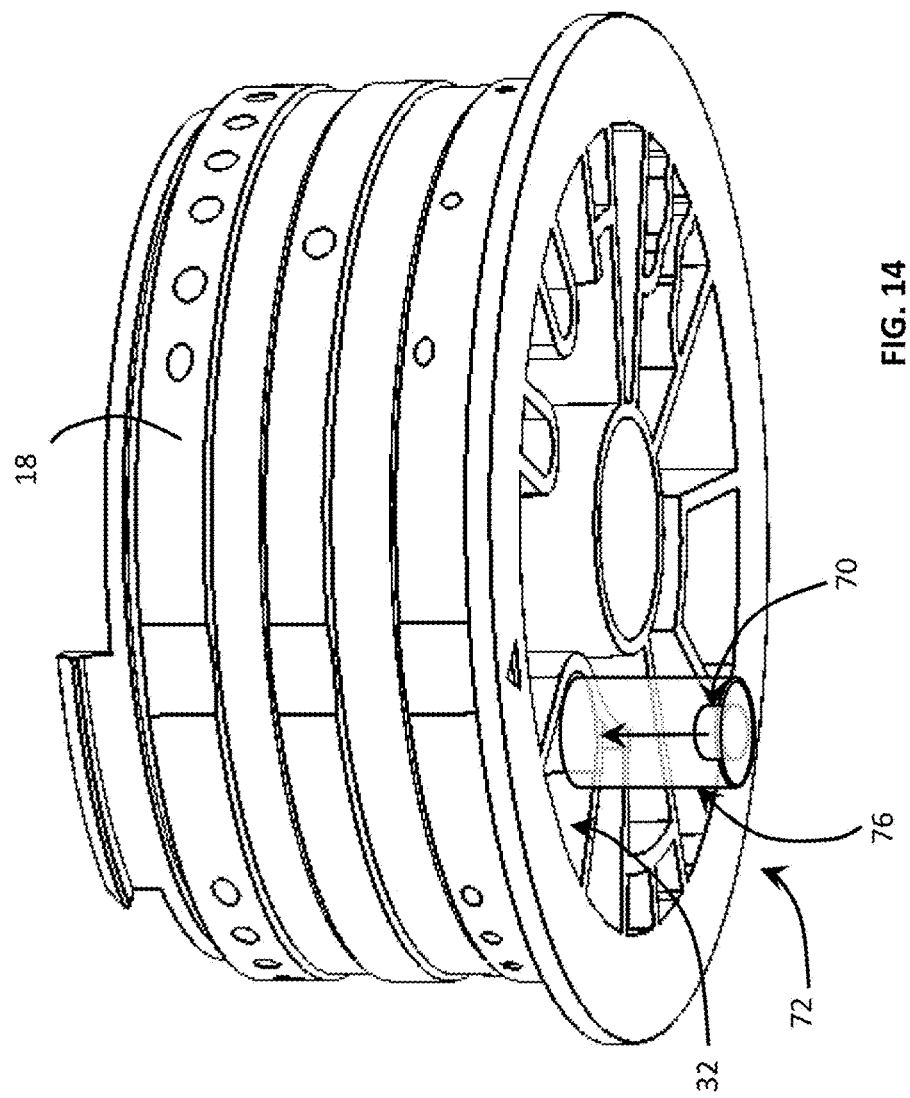
FIG. 14 depicts an isolated perspective view of an overturned cartridge rotor for receiving the pellet of dried reagent depicted in FIG. 13.
Figure 13:
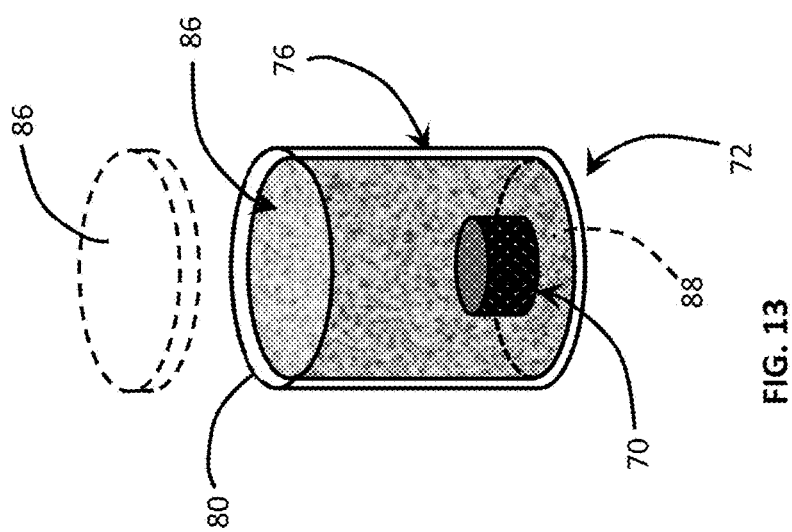
FIG. 13 depicts an isolated perspective view of a cap holding a pellet of dried reagent for being received within an assay chamber of the disposable cartridge.

In FIGS. 13 and 14, the cap 76 may include an open end 86 for receiving the pellet 70 of dried reagent and a closed end 88 for enclosing the open end of the assay chamber 32. In this embodiment, the cartridge rotor 18 is overturned such that the opening of the respective chamber 32 faces downwardly for receiving an open end 86 of the cap 76. The cap 76 is press-fit into the open end of the chamber 32 thereby enclosing the dried reagent, i.e., dried pellet 70, in the assay chamber 32. While this method does not prevent the pellet 70 of reagent from moving in the chamber 32, it limits contact by an operator with the dried pellet 70 prior to loading within the assay chamber 32.

In another embodiment, the pellet 70 is loaded into the tubular cap 76, filled with an inert gas such as helium or argon, and closed by a detachable cover 86 to retain the pellet 70 along with the gas. In this embodiment, the inert gas functions to reduce oxidation of the dried pellet 70 in a time between initial manufacture and use of the disposable cartridge 20. Consequently, immediately prior to use, the operator removes the detachable cover 86 and press-fits the tubular cap 76 into the assay chamber 32 of the cartridge rotor 18.

Figure 15:
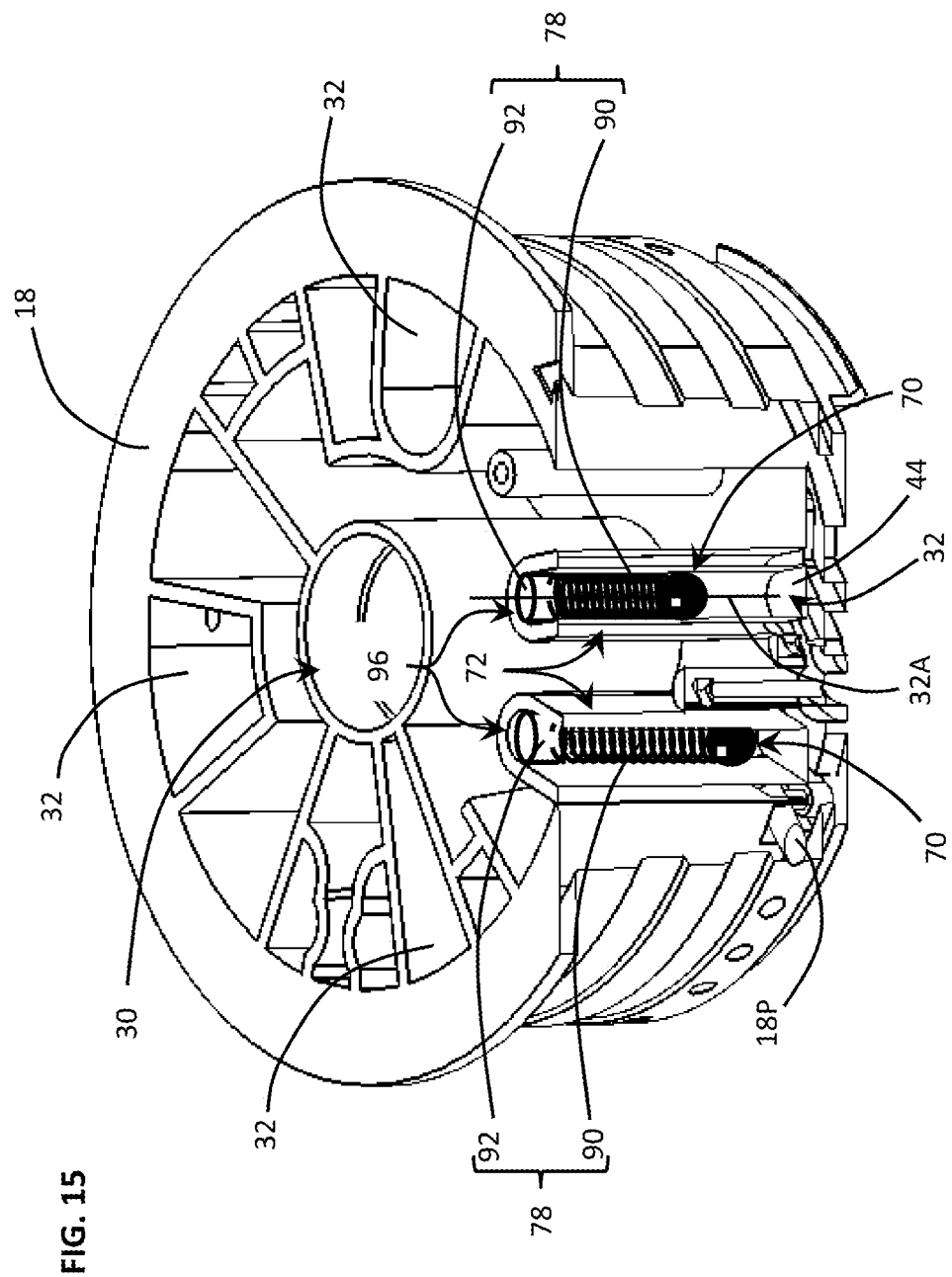
FIG. 15 depicts a broken-away, sectional view of the cartridge rotor wherein an assay chemical, in the form of a pellet, sphere, pill or other dissolvable shape, is spring-biased downwardly, toward a portion of the assay chamber which fills with an assay fluid during one of the mixing steps.

In yet another embodiment depicted in FIG. 15, a plug-spring 78 includes a pellet 70 attached to a spring element 90 which, in turn, is mounted to an end plug 92. More specifically, in this embodiment, the pellet 70 is spherically shaped, however, the pellet 70 may be any shape which facilitates rehydration of the dried reagent 70. The spring element 90 is disposed along the elongate axis 32A of the chamber 32 and, in the described embodiment, is a coil spring 90 having an end loop which cups or circumscribes the spherical surface of the dried pellet 70. Finally, the end plug 92 is cylindrical to engage the open end, or rim 96, of the chamber 32. Consequently, the plug 92 secures the spring element 90 and pellet 70 within the chamber 32, i.e., inhibiting displacement of the pellet 70 while the spring element 90 biases the pellet 70 downwardly, toward the base or bottom 44 of the cartridge rotor 18. The pellet 70 may be biased toward the port 18P through which assay fluids are injected or withdrawn. While the end plug 92 may be solid, it should be appreciated that the end plug 92 may be porous to facilitate fluid flow into and out of the chamber 32.

In summary, the various embodiments described hereinabove provide a method and apparatus for securing a dried, reinforced/unreinforced, reagent within an assay chamber 32 of a disposable cartridge 20. Functionally, the methods minimize or eliminate handling of the dried reagent 60, 70 by operators or assembly personnel. The carrier pod 74 encloses the pellet 70 while providing a fluid by-pass screen or filter to allow rehydration of the dried reagent 70. The removable cover 86 of the cap 76 allows the pellet 70 to be transported within a container 76 which may be oxygen deprived (i.e., replaced by argon or helium) to prevent oxidation in the time between manufacture and use. Finally, the pellet 70 is protected from movement and vibrations induced during transport of the disposable cartridge 20. As such, the propensity for the pellet 70 to break-apart within the chamber 32 is mitigated. That is, there is little or no opportunity for the pellet 70 to crumble within the assay chamber 32 of the disposable cartridge 20.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A method for holding a reagent within a disposable cartridge of a diagnostic assay system, the disposable cartridge having at least one assay chamber for combining assay fluids, comprising the steps of:
   forming a scaffold structure from one of wire, netting, or open-celled foam material in a shape of a portion of the at least one assay chamber;
   mixing a reagent, a binder, and a liquid solvent to produce a liquid reagent-binder;
   impregnating the scaffold structure with the liquid reagent-binder; and
   drying the liquid reagent-binder to remove the liquid solvent therefrom to produce a dried reagent adhered to the scaffold structure that is formed in the shape of the portion of the at least one assay chamber.

2. The method according to claim 1, further comprising the step of:
   placing the scaffold structure into the assay chamber prior to the step of impregnating the scaffold structure with the liquid reagent-binder.

3. The method according to claim 2, wherein the step of placing the scaffold structure into the assay chamber includes the step of:
   placing the scaffold structure into a sump region of the assay chamber that is a portion of the assay chamber disposed in a lower section of the assay chamber.

4. The method according to claim 1, wherein the shape of the portion of the at least one assay chamber corresponds to a sump region of the assay chamber that is a portion of the assay chamber disposed in a lower section of the assay chamber.

5. The method according to claim 1, further comprising the steps of:
   forming the liquid reagent-binder in a mold configured to follow a shape of the assay chamber prior to the step of impregnating the scaffold structure; and
   removing the dried reagent from the mold and bonding the dried reagent to the portion of the at least one assay chamber.

6. The method according to claim 5, wherein the step of bonding the dried reagent includes the step of:
   placing the scaffold structure into a sump region of the assay chamber.

7. The method according to claim 1, further comprising the step of:
   enclosing the dried reagent in a carrier pod having a fluid by-pass filter at one end thereof, and
   placing the carrier pod into the assay chamber,
   wherein the fluid by-pass filter facilitates rehydration of the dried reagent during assay testing.

8. The method according to claim 7, wherein the carrier pod is placed in a sump region of the assay chamber with the fluid by-pass filter facing downwardly into the sump region.

* * * * *